(12) United States Patent
Ceccarelli et al.

(10) Patent No.: US 9,586,903 B2
(45) Date of Patent: Mar. 7, 2017

(54) ISOQUINOLINE DERIVATIVES

(71) Applicant: Hoffmann-La Roche Inc., Little Falls, NJ (US)

(72) Inventors: Simona M. Ceccarelli, Basel (CH); Ravi Jagasia, Loerrach (DE); Roland Jakob-Roetne, Inzlingen (DE); Rainer E. Martin, Basel (CH); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/926,387

(22) Filed: Oct. 29, 2015

(65) Prior Publication Data
US 2016/0046583 A1 Feb. 18, 2016

Related U.S. Application Data

(63) Continuation of application No. PCT/EP2014/058774, filed on Apr. 30, 2014.

(30) Foreign Application Priority Data

May 3, 2013 (EP) .................................. 13166390

(51) Int. Cl.
| | | |
|---|---|---|
| C07D 217/14 | (2006.01) | |
| C07D 405/12 | (2006.01) | |
| A61K 9/00 | (2006.01) | |
| A61K 9/20 | (2006.01) | |
| A61K 9/48 | (2006.01) | |
| A61K 47/10 | (2006.01) | |
| C07D 401/06 | (2006.01) | |
| C07D 401/12 | (2006.01) | |
| C07D 405/04 | (2006.01) | |
| C07D 417/06 | (2006.01) | |
| C07D 217/26 | (2006.01) | |
| C07D 401/04 | (2006.01) | |
| A61K 31/496 | (2006.01) | |
| A61K 31/5377 | (2006.01) | |
| A61K 31/541 | (2006.01) | |
| A61K 31/472 | (2006.01) | |
| A61K 31/4725 | (2006.01) | |

(52) U.S. Cl.
CPC .......... *C07D 217/14* (2013.01); *A61K 9/0019* (2013.01); *A61K 9/2018* (2013.01);
(Continued)

(58) Field of Classification Search
None
See application file for complete search history.

(56) References Cited

U.S. PATENT DOCUMENTS

2012/0040936 A1 2/2012 Kanno et al.
2012/0142727 A1 6/2012 Kinoyama et al.

FOREIGN PATENT DOCUMENTS

WO WO 2010/116915 A1 * 10/2010 ........... C07D 217/14

OTHER PUBLICATIONS

Database CAPLUS in STN, Acc. No. 2010:1281989, Kanno et al., WO 2010116915 A1 (Oct. 14, 2010) (abstract).*
ISR for PCT/EP 2014/058774, mailed Jun. 5, 2014.
Savendahl Lars,Database medline (Online) US National Library of Medicine (NLM), Bethesda, MD, US; Oct. 23, 2012, Savendahl Lars: 'The effect of acute and chronic stress on growth.' Database accession No. NLM23092892.

*Primary Examiner* — Brian J Davis

(57) ABSTRACT

The present invention relates to the use of compounds of general formula

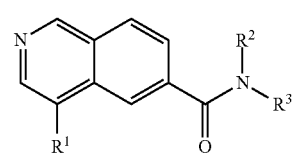

wherein
$R^1$ is phenyl or pyridinyl, which are optionally substituted by halogen, cyano or lower alkyl substituted by halogen, or is dihydro-pyran-4-yl;
$R^2$ is hydrogen or lower alkyl;
$R^3$ is —(CHR)$_n$-phenyl, optionally substituted by lower alkoxy or S(O)$_2$-lower alkyl,
   or is heterocycloalkyl, optionally substituted by =O and lower alkyl,
   or is —(CH$_2$)$_n$-five or six membered heteroaryl, optionally substituted by lower alkyl,
   or is hydrogen, lower alkyl, lower alkyl substituted by halogen, lower alkyl substituted by hydroxy, —NR—S(O)$_2$-lower alkyl, —(CH$_2$)$_n$-cycloalkyl or —(CH$_2$)$_n$—S(O)$_2$-lower alkyl; or
$R^2$ and $R^3$ form together with the N-atom to which they are attached a heterocycloalkyl ring, selected from the group consisting of 1,1-dioxo-thiomorpholinyl, morpholinyl, or pyrrolidinyl, optionally substituted by hydroxyl;
R is hydrogen or lower alkyl;
n is 0, 1 or 2;
or to a pharmaceutically acceptable acid addition salt, to a racemic mixture or to its corresponding enantiomer and/or optical isomers thereof,
for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuroactive drugs, such as alcohol, opiates, methamphetamine, phencyclidine or cocaine.

9 Claims, No Drawings

(52) U.S. Cl.
CPC .......... *A61K 9/2054* (2013.01); *A61K 9/2059* (2013.01); *A61K 9/4858* (2013.01); *A61K 9/4866* (2013.01); *A61K 31/472* (2013.01); *A61K 31/4725* (2013.01); *A61K 31/496* (2013.01); *A61K 31/5377* (2013.01); *A61K 31/541* (2013.01); *A61K 47/10* (2013.01); *C07D 217/26* (2013.01); *C07D 401/04* (2013.01); *C07D 401/06* (2013.01); *C07D 401/12* (2013.01); *C07D 405/04* (2013.01); *C07D 405/12* (2013.01); *C07D 417/06* (2013.01)

\* cited by examiner

ISOQUINOLINE DERIVATIVES

CROSS REFERENCE TO RELATED APPLICATIONS

This application is a continuation of International Application No. PCT/EP2014/058774 having an international filing date of Apr. 30, 2014, which claims benefit of priority under 35 U.S.C. §119 to European Patent Application No. 13166390.8 filed May 3, 2013, both of which are incorporated herein by reference in their entirety.

The present invention relates to the use of compounds of general formula

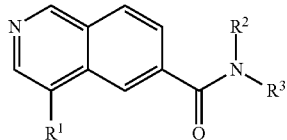

wherein
$R^1$ is phenyl or pyridinyl, which are optionally substituted by halogen, cyano or lower alkyl substituted by halogen, or is dihydro-pyran-4-yl;
$R^2$ is hydrogen or lower alkyl;
$R^3$ is —(CHR)$_n$-phenyl, optionally substituted by lower alkoxy or S(O)$_2$-lower alkyl, or is heterocycloalkyl, optionally substituted by =O and lower alkyl, or is —(CH$_2$)$_n$-five or six membered heteroaryl, optionally substituted by lower alkyl, or is hydrogen, lower alkyl, lower alkyl substituted by halogen, lower alkyl substituted by hydroxy, —NR—S(O)$_2$-lower alkyl, —(CH$_2$)$_n$-cycloalkyl or —(CH$_2$)$_n$—S(O)$_2$-lower alkyl; or
$R^2$ and $R^3$ form together with the N-atom to which they are attached a heterocycloalkyl ring, selected from the group consisting of 1,1-dioxo-thiomorpholinyl, morpholinyl, or pyrrolidinyl, optionally substituted by hydroxy;
R is hydrogen or lower alkyl;
n is 0, 1 or 2;
or to a pharmaceutically acceptable acid addition salt, to a racemic mixture or to its corresponding enantiomer and/or optical isomers thereof,
for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine.

Similar compounds with an isoquinoline core structure are described in WO2010/116915 having a bone formation promoting effect.

Now it has been shown that the present compounds stimulate neurogenesis from neural stem cells (NSCs). Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

The stimulation of adult neurogenesis represents also a therapeutic target for optic neuropathy (S. Isenmann, A. Kretz, A. Cellerino, Progress in Retinal and Eye Research, 22, (2003) 483) and macular degeneration (G. Landa, O. Butovsky, J. Shoshani, M. Schwartz, A. Pollack, Current Eye Research 33, (2008) 1011).

Hence, chemical stimulation of adult neurogenesis offers new regenerative avenues and opportunities to develop novel drugs for treating neurological diseases and neuropsychiatric disorders.

Therefore, the object of the present invention was to identify compounds that modulate neurogenesis. It has been found that the compounds of formula I are active in this area and they may therefore be used for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine.

The most preferred indications for compounds of formula I are Alzheimer's disease, depression, anxiety disorders and stroke.

One embodiment of the invention is the use of compounds of formula I for the treatment of the above-mentioned diseases. The compounds are listed in Tables 1 and 2. These are the compounds N-benzyl-4-(pyridin-4-yl)isoquinoline-6-carboxamide
N-benzyl-4-(4-chlorophenyl)isoquinoline-6-carboxamide
[4-(4-chloro-phenyl)-isoquinolin-6-yl]-(1,1-dioxo-thiomorpholin-4-yl)-methanone
4-(4-chloro-phenyl)-isoquinoline-6-carboxylic acid (2,2-dimethyl-propyl)-amide
4-(4-chlorophenyl)-N-cyclopropylisoquinoline-6-carboxamide
4-(4-chlorophenyl)-N-(cyclopropylmethyl)isoquinoline-6-carboxamide
4-(4-chlorophenyl)-N-(2-(methylsulfonyl)ethyl)isoquinoline-6-carboxamide
4-(4-chlorophenyl)-N-(pyridin-3-ylmethyl)isoquinoline-6-carboxamide
4-(4-chlorophenyl)-N-(4-(methylsulfonyl)benzyl)isoquinoline-6-carboxamide
4-(4-chlorophenyl)-N-(2-methoxybenzyl)isoquinoline-6-carboxamide
4-(4-chlorophenyl)-N-(pyridin-2-ylmethyl)isoquinoline-6-carboxamide
4-(4-chlorophenyl)-N-(3-(methylsulfonyl)benzyl)isoquinoline-6-carboxamide
4-(4-chlorophenyl)-N-phenylisoquinoline-6-carboxamide
4-(4-chlorophenyl)-N-(2,2,2-trifluoroethyl)isoquinoline-6-carboxamide
4-(4-chlorophenyl)-N-isopropylisoquinoline-6-carboxamide
4-(4-chlorophenyl)-N-(tetrahydrofuran-3-yl)isoquinoline-6-carboxamide
4-(4-chlorophenyl)-N-(1-hydroxy-2-methylpropan-2-yl)isoquinoline-6-carboxamide
(4-(4-chlorophenyl)isoquinolin-6-yl)(morpholino)methanone
(4-(4-chlorophenyl)isoquinolin-6-yl)(4-methylpiperazin-1-yl)methanone
4-(4-chlorophenyl)-N-((2-methyl-5-oxopyrrolidin-2-yl)methyl)isoquinoline-6-carboxamide
4-(4-chlorophenyl)-N-(cyclopropylmethyl)-N-methylisoquinoline-6-carboxamide
(4-(4-chlorophenyl)isoquinolin-6-yl)(3-hydroxypyrrolidin-1-yl)methanone
N-tert-butyl-4-(4-chlorophenyl)isoquinoline-6-carboxamide
4-(4-chlorophenyl)-N-(3,3,3-trifluoropropyl)isoquinoline-6-carboxamide
N'-(4-(4-chlorophenyl)isoquinoline-6-carbonyl)methanesulfonohydrazide
4-(4-chlorophenyl)-N-(1-methyl-1H-pyrazol-4-yl)isoquinoline-6-carboxamide
4-(4-chlorophenyl)-N-(1-(3-(methylsulfonyl)phenyl)ethyl)isoquinoline-6-carboxamide
N'-(4-(4-chlorophenyl)isoquinoline-6-carbonyl)-N-methylmethanesulfonohydrazide
4-(3,6-dihydro-2H-pyran-4-yl)isoquinoline-6-carboxamide
4-(4-cyanophenyl)isoquinoline-6-carboxamide
4-(2,4-dichlorophenyl)isoquinoline-6-carboxamide
4-(6-chloropyridin-3-yl)isoquinoline-6-carboxamide
4-(4-chlorophenyl)isoquinoline-6-carboxamide (CAS1248555-68-1) and
4-(4-(trifluoromethyl)phenyl)isoquinoline-6-carboxamide (CAS1248554-05-3).

The present invention relates also to novel compounds of formulas I-1 and 1-2 and to specific novel compounds of formula I, to the processes for their production, as well as to the use of compound of formula I in the treatment of disorders, relating to neurogenesis, depression, anxiety disorders, Parkinson's disease, dementia, Alzheimer's disease, Down syndrome, autism spectrum disorders, amyotrophic lateral sclerosis, multiple sclerosis and Huntington's disease and to pharmaceutical compositions containing the novel compounds of formula I.

One embodiment of the invention are new compounds of formula I, which compounds are N-benzyl-4-(pyridin-4-yl)isoquinoline-6-carboxamide
N-benzyl-4-(4-chlorophenyl)isoquinoline-6-carboxamide
[4-(4-chloro-phenyl)-isoquinolin-6-yl]-(1,1-dioxo-thiomorpholin-4-yl)-methanone
4-(4-chloro-phenyl)-isoquinoline-6-carboxylic acid (2,2-dimethyl-propyl)-amide
4-(4-chlorophenyl)-N-cyclopropylisoquinoline-6-carboxamide
4-(4-chlorophenyl)-N-(cyclopropylmethyl)isoquinoline-6-carboxamide
4-(4-chlorophenyl)-N-(2-(methylsulfonyl)ethyl)isoquinoline-6-carboxamide
4-(4-chlorophenyl)-N-(pyridin-3-ylmethyl)isoquinoline-6-carboxamide
4-(4-chlorophenyl)-N-(4-(methylsulfonyl)benzyl)isoquinoline-6-carboxamide
4-(4-chlorophenyl)-N-(2-methoxybenzyl)isoquinoline-6-carboxamide
4-(4-chlorophenyl)-N-(pyridin-2-ylmethyl)isoquinoline-6-carboxamide
4-(4-chlorophenyl)-N-(3-(methylsulfonyl)benzyl)isoquinoline-6-carboxamide
4-(4-chlorophenyl)-N-phenylisoquinoline-6-carboxamide
4-(4-chlorophenyl)-N-(2,2,2-trifluoroethyl)isoquinoline-6-carboxamide
4-(4-chlorophenyl)-N-isopropylisoquinoline-6-carboxamide
4-(4-chlorophenyl)-N-(tetrahydrofuran-3-yl)isoquinoline-6-carboxamide
4-(4-chlorophenyl)-N-(1-hydroxy-2-methylpropan-2-yl)isoquinoline-6-carboxamide
(4-(4-chlorophenyl)isoquinolin-6-yl)(morpholino)methanone (4-(4-chlorophenyl)isoquinolin-6-yl)(4-methylpiperazin-1-yl)methanone 4-(4-chlorophenyl)-N-((2-methyl-5-oxopyrrolidin-2-yl)methyl)isoquinoline-6-carboxamide 4-(4-chlorophenyl)-N-(cyclopropylmethyl)-N-methylisoquinoline-6-carboxamide (4-(4-chlorophenyl)isoquinolin-6-yl)(3-hydroxypyrrolidin-1-yl)methanone N-tert-butyl-4-(4-chlorophenyl)isoquinoline-6-carboxamide 4-(4-chlorophenyl)-N-(3,3,3-trifluoropropyl)isoquinoline-6-carboxamide N'-(4-(4-chlorophenyl)isoquinoline-6-carbonyl)methanesulfonohydrazide 4-(4-chlorophenyl)-N-(1-methyl-1H-pyrazol-4-yl)isoquinoline-6-carboxamide 4-(4-chlorophenyl)-N-(1-(3-(methylsulfonyl)phenyl)ethyl)isoquinoline-6-carboxamide N'-(4-(4-chlorophenyl)isoquinoline-6-carbonyl)-N-methyl-methanesulfonohydrazide 4-(3,6-dihydro-2H-pyran-4-yl)isoquinoline-6-carboxamide 4-(4-cyanophenyl)isoquinoline-6-carboxamide 4-(2,4-dichlorophenyl)isoquinoline-6-carboxamide or 4-(6-chloropyridin-3-yl)isoquinoline-6-carboxamide.

One object of the present invention are compounds of formula I-1

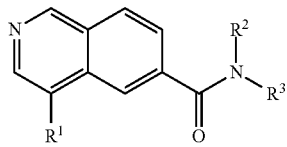

I-1 wherein

R$^1$ is pyridinyl, which is optionally substituted by halogen, cyano or lower alkyl substituted by halogen, or is dihydro-pyran-4-yl;

R$^2$ is hydrogen or lower alkyl;

R$^3$ is —(CHR)$_n$-phenyl, optionally substituted by lower alkoxy or S(O)$_2$-lower alkyl, or is heterocycloalkyl, optionally substituted by =O and lower alkyl, or is —(CH$_2$)$_n$-five or six membered heteroaryl, optionally sunbstituted by lower alkyl, or is hydrogen, lower alkyl, lower alkyl substituted by halogen, lower alkyl substituted by hydroxy, —NR—S(O)$_2$-lower alkyl, —(CH$_2$)$_n$-cycloalkyl or —(CH$_2$)$_n$—S(O)$_2$-lower alkyl; or R$^2$ and R$^3$ form together with the N-atom to which they are attached a heterocycloalkyl ring, selected from the group consisting of 1,1-dioxo-thiomorpholinyl, morpholinyl, or pyrrolidinyl, optionally substituted by hydroxyl;

R is hydrogen or lower alkyl;

n is 0, 1 or 2;

or a pharmaceutically acceptable acid addition salt, a racemic mixture or its corresponding enantiomer and/or optical isomers thereof, for example the following compounds N-benzyl-4-(pyridin-4-yl)isoquinoline-6-carboxamide 4-(3,6-dihydro-2H-pyran-4-yl)isoquinoline-6-carboxamide or 4-(6-chloropyridin-3-yl)isoquinoline-6-carboxamide.

One further object of the present invention are compounds of formula I-2

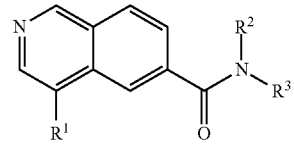

I-2 wherein

R$^1$ is phenyl or pyridinyl, which are optionally substituted by halogen, cyano or lower alkyl substituted by halogen, or is dihydro-pyran-4-yl;

R$^2$ and R$^3$ form together with the N-atom to which they are attached a heterocycloalkyl ring, selected from the group consisting of 1,1-dioxo-thiomorpholinyl, morpholinyl, or pyrrolidinyl, optionally substituted by hydroxyl;

R is hydrogen or lower alkyl;

n is 0, 1 or 2;

or a pharmaceutically acceptable acid addition salt, a racemic mixture or its corresponding enantiomer and/or optical isomers thereof, for example the following compounds

[4-(4-chloro-phenyl)-isoquinolin-6-yl]-(1,1-dioxo-thiomorpholin-4-yl)-methanone (4-(4-chlorophenyl)isoquinolin-6-yl)(morpholino)methanone (4-(4-chlorophenyl)isoquinolin-6-yl)(4-methylpiperazin-1-yl)methanone or (4-(4-chlorophenyl)isoquinolin-6-yl)(3-hydroxypyrrolidin-1-yl)methanone.

One further embodiment of the invention is a pharmaceutical composition comprising a novel compound falling into the scope of formula I, which compounds are listed in Table 1.

One embodiment of the present invention is the use of a compound of formula I for the preparation of medicaments for the therapeutic treatment of depression, anxiety disorders, Parkinson's disease, dementia, Alzheimer's disease, Down syndrome, autism spectrum disorders, amyotrophic lateral sclerosis, multiple sclerosis and Huntington's disease, which compounds are listed in Tables 1 and 2.

A further embodiment of the invention is a method for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine which method comprises administering an effective amount of a compound of formula I, for example compounds disclosed in Tables 1 and 2.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "lower alkyl substituted by halogen" denotes a lower alkyl group as defined above, wherein at least one hydrogen atom is replaced by a halogen atom. The preferred group is CF$_3$.

The term "lower alkyl substituted by hydroxy" denotes a lower alkyl group as defined above, wherein at least one hydrogen atom is replaced by a hydroxy atom.

The term "heterocycloalkyl" comprises non aromatic rings, containing at least one heteroatom, selected from N, O or S. Such groups are tetrahydofuranyl, piperidinyl, morpholinyl, pyrrolidinyl, piperazinyl or 1,1-di-oxo-thiomorpholinyl.

The term "five or six membered heteroaryl" comprises aromatic rings, containing at least one heteroatom, selected from N, O or S. Such groups are pyridinyl, imidazolyl, pyrazolyl, pyrazinyl, pyrimidinyl or thiazolyl.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The present new compounds of formula I and their pharmaceutically acceptable salts can be prepared by methods known in the art, for example, by processes described below, which process comprises a) reacting a compound of formula

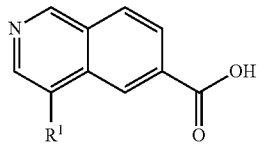

1 with a compound of formula

NHR$^2$R$^3$   2 to a compound of formula

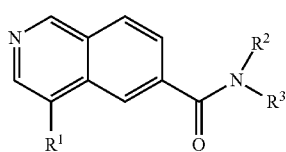

I and, if desired, converting the compounds obtained into pharmaceutically acceptable acid addition salts, or b) reacting a compound of formula 3

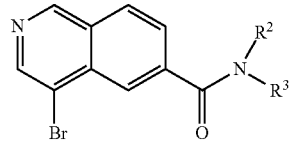

3 with a compound of formula

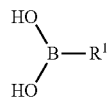

4 to a compound of formula

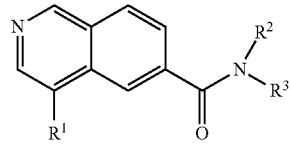

I and, if desired, converting the compounds obtained into pharmaceutically acceptable acid addition salts, wherein the substituents are as described as above.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

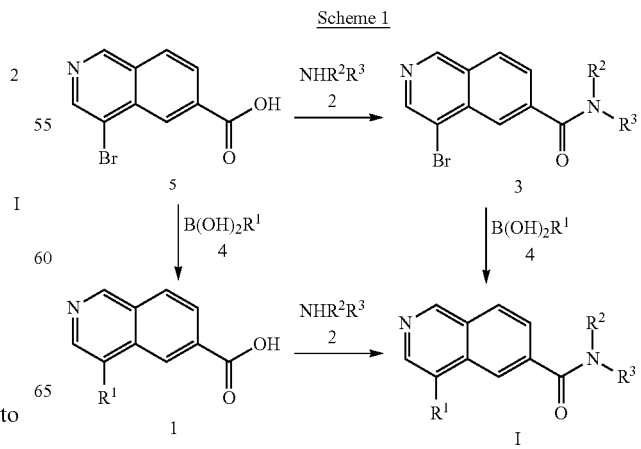

A mixture of 4-bromo-isoquinoline-6-carboxylic acid of formula 5, N,N-diisopropylethylamine and O-(7-azabenzotriazol-1-yl)-N,N,N',N'-tetramethyluronium hexafluorophosphate (HATU) in dimethylformamide is stirred at room temperature for 10 minutes. The corresponding amine of formula 2 is added and stirring is continued over two day to yield a compound of formula 3.

Furthermore, to a suspension of 4-bromo-isoquinoline-6-carboxylic acid amide of formula 3 and a boronic acid of formula 4 and cesium carbonate in dioxane and water is added bis(diphenylphosphino)ferrocene-palladium(II)dichloride. The mixture is stirred at 80° C. for 3 hours. Removal of the solvent by distillation and chromatography yields the compound of formula I.

Amide bond formation reactions can be conducted using either batch or by employing continuous mode (flow) reaction protocols. Continuous mode synthesis is conducted using a custom-made, integrated flow synthesis and preparative HPLC purification system. A commercial R4 flow reactor module from Vapourtec is connected to a preparative HPLC purification system that is assembled from of a Gilson LH 215 auto-sampler, two Gilson 819 injection modules, two Agilent 1100 Series pumps, one Agilent 1200 series DADA detector, two Varian prep star pumps, one Dionex UV detector, one Polymer Laboratory light-scattering detector and one Dionex P-680 pump. Reagents and starting materials are injected via the LH 215 auto-sampler onto the flow reactor reagent loops (Gilson 819 injection modules) and from there onto the PFA (perfluoroalkoxy polymer) tube reactor coil (10 mL) fitted with a 100 psi back pressure regulator (BPR). In order to limit dispersion effects and to maintain a consistent concentration within the reaction zone as it progresses through the flow reactor, small air bubbles are injected before and after the reaction segment. After completion of the flow reaction, the crude reaction mixture is directly loaded onto the preparative HPLC injection loop to undergo HPLC purification. Purified compounds are collected via the LH 215 auto-sampler. The entire process is controlled using the chromatography management system software Chromeleon version 6.80 from Dionex.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21'000 cells/cm$^2$ in a media volume of 38 µl.

4 hours after cell seeding, compound solutions are added at a volume of 2 µl. Stock solutions of the compounds (water, 5% DMSO) are diluted to obtain a dose response (11 points, dilution factor is 2), ranging from 8 µM to 8 nM. Controls are run to consistently determine the neurogenic properties of the cells:

Negative (neutral) control is cell culture Media (final DMSO concentration: 0.25%).

Positive controls are:

1. cell culture Media+100 ng/ml FGF2 (final DMSO concentration: 0.1%)

2. cell culture Media+20 ng/ml EGF (final DMSO concentration: 0.1%)

3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (UltraGlo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The EC150 is the compound concentration at which 150% activity of control (100%) is reached. The preferred compounds show a $EC_{150}$ (μM) in the range of <2.5 μM as shown in Table 1 below.

Pharmaceutical Compositions

The compounds of formula I as well as their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Examples of compositions according to the invention are, but are not limited to:

Tablets of the following composition are manufactured in the usual manner:

|  | mg/tablet | | | |
| --- | --- | --- | --- | --- |
| ingredient | 5 | 25 | 100 | 500 |
| 1. compound of formula I | 5 | 25 | 100 | 500 |
| 2. lactose | 45 | 105 | 30 | 150 |
| 3. corn starch | 15 | 6 | 6 | 60 |
| 4. microcrystalline cellulose | 34 | 30 | 30 | 450 |
| 5. magnesium stearate | 1 | 1 | 1 | 1 |
| total | 100 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

|  | mg/capsule | | | | |
| --- | --- | --- | --- | --- | --- |
| ingredient | 5 | 10 | 25 | 100 | 500 |
| 1. compound of formula I | 5 | 10 | 25 | 100 | 500 |
| 2. lactose | 159 | 155 | 123 | 148 | — |
| 3. corn starch | 25 | 30 | 35 | 40 | 70 |
| 4. talc | 10 | 5 | 15 | 10 | 25 |
| 5. magnesium stearate | 1 | — | 2 | 2 | 5 |
| total | 200 | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatin capsules.

Injection solutions of the following composition are manufactured:

| ingredient | mg/injection solution. |
| --- | --- |
| compound of formula I | 3 |
| polyethylene Glycol 400 | 150 |
| acetic acid | q.s. ad pH 5.0 |
| water for injection solutions | ad 1.0 ml |

Manufacturing Procedure

The compounds of formulas I are dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

TABLE 1

List of examples and EC$_{150}$ data of novel compounds

| Example | Structure | Name | EC$_{150}$ (uM) |
|---|---|---|---|
| 1 | 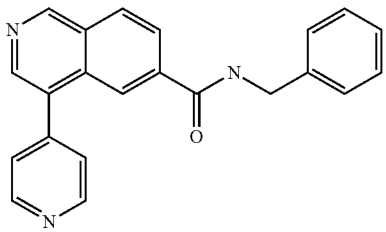 [SMILES: O=C(NCc1ccccc1)c1ccc2cncc(-c3ccncc3)c2c1] | N-Benzyl-4-(pyridin-4-yl)isoquinoline-6-carboxamide | 0.07 |
| 2 | 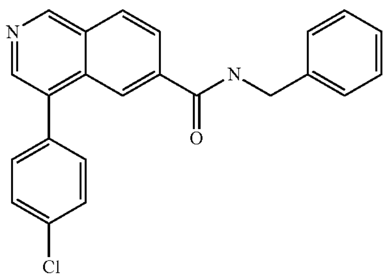 [SMILES: O=C(NCc1ccccc1)c1ccc2cncc(-c3ccc(Cl)cc3)c2c1] | N-benzyl-4-(4-chlorophenyl)isoquinoline-6-carboxamide | 0.09 |
| 3 | 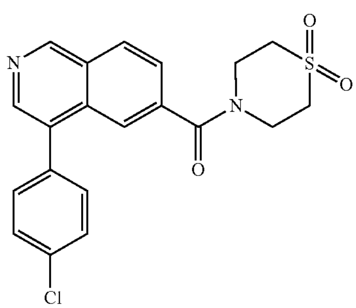 [SMILES: O=C(c1ccc2cncc(-c3ccc(Cl)cc3)c2c1)N1CCS(=O)(=O)CC1] | [4-(4-Chloro-phenyl)-isoquinolin-6-yl]-(1,1-dioxo-thiomorpholin-4-yl)-methanone | 0.16 |
| 4 | 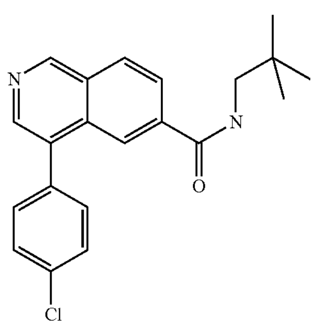 [SMILES: CC(C)(C)CNC(=O)c1ccc2cncc(-c3ccc(Cl)cc3)c2c1] | 4-(4-Chloro-phenyl)-isoquinoline-6-carboxylic acid (2,2-dimethyl-propyl)-amide | 0.19 |
| 5 | 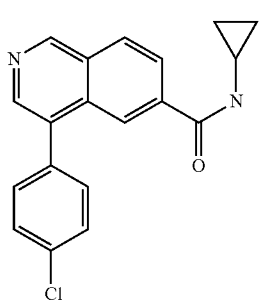 [SMILES: O=C(NC1CC1)c1ccc2cncc(-c3ccc(Cl)cc3)c2c1] | 4-(4-Chlorophenyl)-N-cyclopropylisoquinoline-6-carboxamide | 0.03 |

TABLE 1-continued

List of examples and EC₁₅₀ data of novel compounds

| Example | Structure | Name | EC₁₅₀ (uM) |
|---|---|---|---|
| 6 | 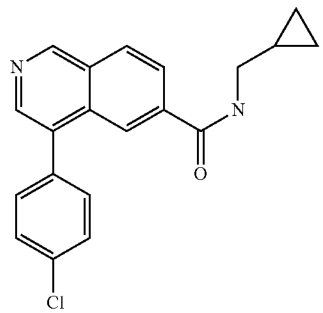 [SMILES: O=C(NCC1CC1)c1ccc2cncc(-c3ccc(Cl)cc3)c2c1] | 4-(4-Chlorophenyl)-N-(cyclopropylmethyl)isoquinoline-6-carboxamide | 0.19 |
| 7 | 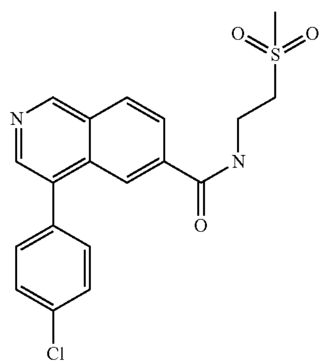 [SMILES: CS(=O)(=O)CCNC(=O)c1ccc2cncc(-c3ccc(Cl)cc3)c2c1] | 4-(4-Chlorophenyl)-N-(2-(methylsulfonyl)ethyl)isoquinoline-6-carboxamide | 0.07 |
| 8 | 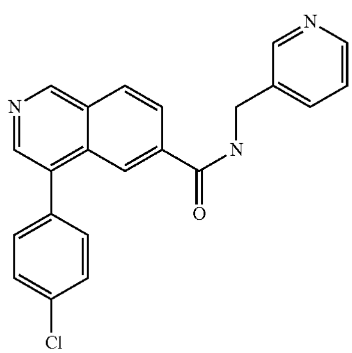 [SMILES: O=C(NCc1cccnc1)c1ccc2cncc(-c3ccc(Cl)cc3)c2c1] | 4-(4-Chlorophenyl)-N-(pyridin-3-ylmethyl)isoquinoline-6-carboxamide | 0.08 |
| 9 | 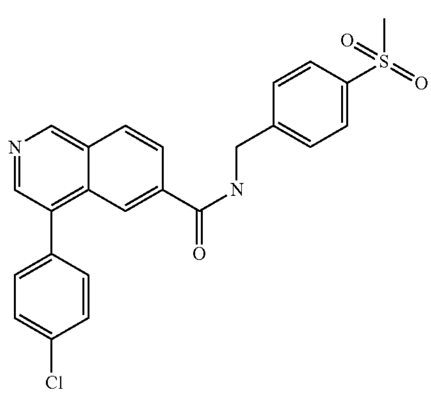 [SMILES: CS(=O)(=O)c1ccc(CNC(=O)c2ccc3cncc(-c4ccc(Cl)cc4)c3c2)cc1] | 4-(4-chlorophenyl)-N-(4-(methylsulfonyl)benzyl)isoquinoline-6-carboxamide | 0.85 |

TABLE 1-continued

List of examples and EC$_{150}$ data of novel compounds

| Example | Name | EC$_{150}$ (uM) |
|---|---|---|
| 10 | 4-(4-Chlorophenyl)-N-(2-methoxybenzyl)isoquinoline-6-carboxamide | 0.09 |
| 11 | 4-(4-Chlorophenyl)-N-(pyridin-2-ylmethyl)isoquinoline-6-carboxamide | 0.09 |
| 12 | 4-(4-Chlorophenyl)-N-(3-(methylsulfonyl)benzyl)isoquinoline-6-carboxamide | 0.10 |
| 13 | 4-(4-Chlorophenyl)-N-phenylisoquinoline-6-carboxamide | 0.71 |

TABLE 1-continued

List of examples and EC$_{150}$ data of novel compounds

| Example | Structure | Name | EC$_{150}$ (uM) |
|---|---|---|---|
| 14 | 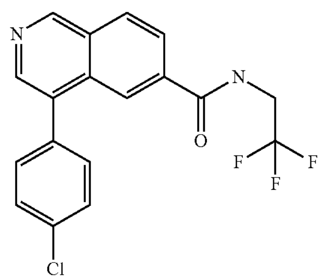 [SMILES: O=C(NCC(F)(F)F)c1ccc2cncc(-c3ccc(Cl)cc3)c2c1] | 4-(4-Chlorophenyl)-N-(2,2,2-trifluoroethyl)isoquinoline-6-carboxamide | 0.05 |
| 15 | 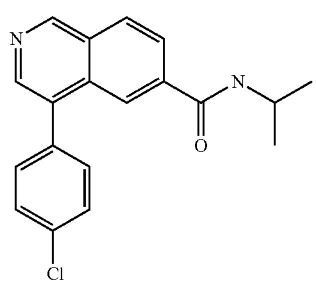 [SMILES: CC(C)NC(=O)c1ccc2cncc(-c3ccc(Cl)cc3)c2c1] | 4-(4-Chlorophenyl)-N-isopropylisoquinoline-6-carboxamide | 0.98 |
| 16 | 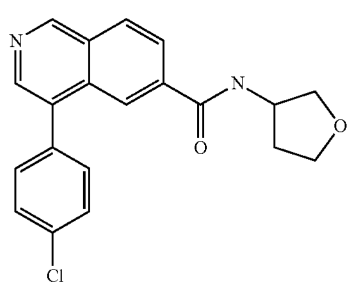 [SMILES: O=C(NC1CCOC1)c1ccc2cncc(-c3ccc(Cl)cc3)c2c1] | 4-(4-Chlorophenyl)-N-(tetrahydrofuran-3-yl)isoquinoline-6-carboxamide | 0.76 |
| 17 | 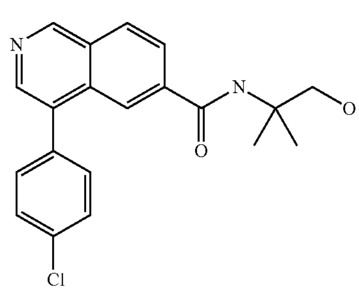 [SMILES: CC(C)(CO)NC(=O)c1ccc2cncc(-c3ccc(Cl)cc3)c2c1] | 4-(4-Chlorophenyl)-N-(1-hydroxy-2-methylpropan-2-yl)isoquinoline-6-carboxamide | 2.50 |
| 18 | 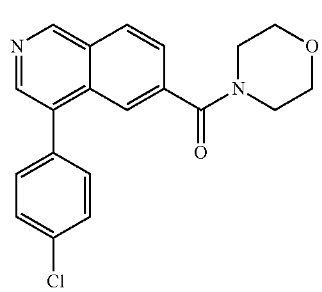 [SMILES: O=C(c1ccc2cncc(-c3ccc(Cl)cc3)c2c1)N1CCOCC1] | (4-(4-Chlorophenyl)isoquinolin-6-yl)(morpholino)methanone | 0.38 |

TABLE 1-continued

List of examples and EC$_{150}$ data of novel compounds

| Example | Structure | Name | EC$_{150}$ (uM) |
|---|---|---|---|
| 19 | 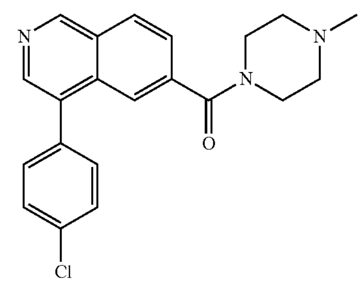 [SMILES: CN1CCN(C(=O)c2ccc3cncc(-c4ccc(Cl)cc4)c3c2)CC1] | (4-(4-Chlorophenyl)isoquinolin-6-yl)(4-methylpiperazin-1-yl)methanone | 0.11 |
| 20 | 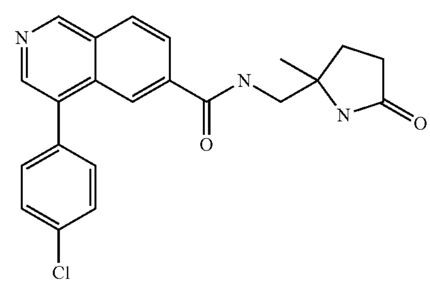 [SMILES: CC1(CNC(=O)c2ccc3cncc(-c4ccc(Cl)cc4)c3c2)CCC(=O)N1] | 4-(4-Chlorophenyl)-N-((2-methyl-5-oxopyrrolidin-2-yl)methyl)isoquinoline-6-carboxamide | 0.18 |
| 21 | 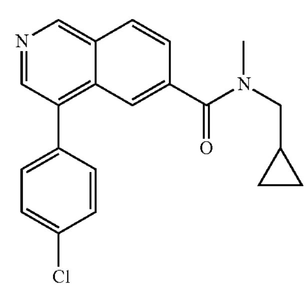 [SMILES: CN(CC1CC1)C(=O)c1ccc2cncc(-c3ccc(Cl)cc3)c2c1] | 4-(4-Chlorophenyl)-N-(cyclopropylmethyl)-N-methylisoquinoline-6-carboxamide | 0.21 |
| 22 | 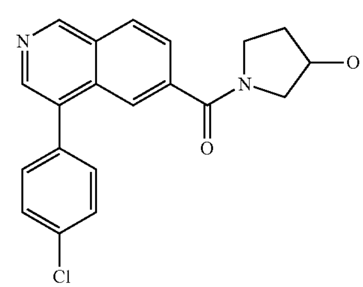 [SMILES: O=C(c1ccc2cncc(-c3ccc(Cl)cc3)c2c1)N1CCC(O)C1] | (4-(4-Chlorophenyl)isoquinolin-6-yl)(3-hydroxypyrrolidin-1-yl)methanone | 0.28 |
| 23 | 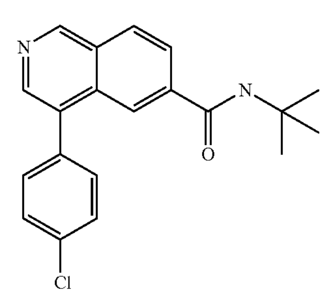 [SMILES: CC(C)(C)NC(=O)c1ccc2cncc(-c3ccc(Cl)cc3)c2c1] | N-tert-Butyl-4-(4-chlorophenyl)isoquinoline-6-carboxamide | 0.73 |

US 9,586,903 B2

TABLE 1-continued

List of examples and EC$_{150}$ data of novel compounds

| Example | Structure | Name | EC$_{150}$ (uM) |
|---|---|---|---|
| 24 | 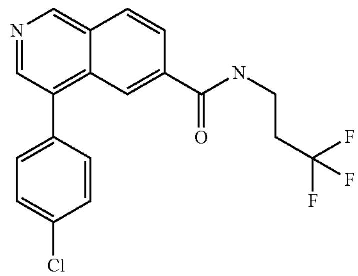 [SMILES: O=C(NCCC(F)(F)F)c1ccc2cncc(-c3ccc(Cl)cc3)c2c1] | 4-(4-Chlorophenyl)-N-(3,3,3-trifluoropropyl)isoquinoline-6-carboxamide | 0.06 |
| 25 | 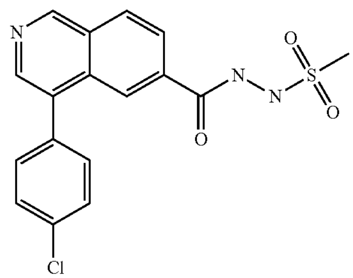 [SMILES: CS(=O)(=O)NNC(=O)c1ccc2cncc(-c3ccc(Cl)cc3)c2c1] | N'-(4-(4-Chlorophenyl)isoquinoline-6-carbonyl)methanesulfonohydrazide | 0.02 |
| 26 | 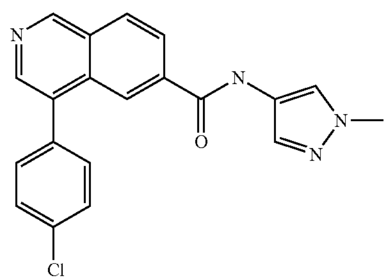 [SMILES: Cn1cc(NC(=O)c2ccc3cncc(-c4ccc(Cl)cc4)c3c2)cn1] | 4-(4-Chlorophenyl)-N-(1-methyl-1H-pyrazol-4-yl)isoquinoline-6-carboxamide | 0.32 |
| 27 | 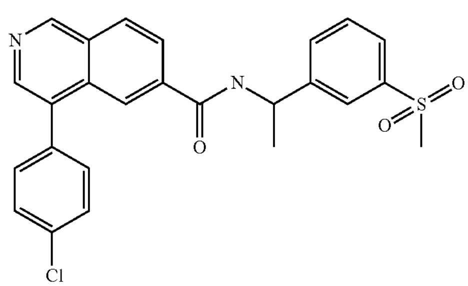 [SMILES: CC(NC(=O)c1ccc2cncc(-c3ccc(Cl)cc3)c2c1)c1cccc(S(C)(=O)=O)c1] | 4-(4-Chlorophenyl)-N-(1-(3-methylsulfonyl)phenyl)ethyl)isoquinoline-6-carboxamide | 0.79 |
| 28 | 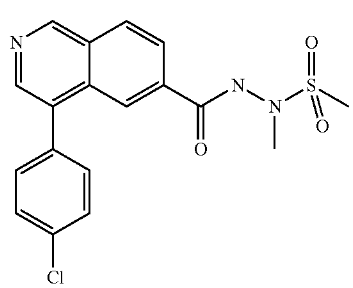 [SMILES: CN(NC(=O)c1ccc2cncc(-c3ccc(Cl)cc3)c2c1)S(C)(=O)=O] | N'-(4-(4-Chlorophenyl)isoquinoline-6-carbonyl)-N-methylmethanesulfonohydrazide | 0.39 |

TABLE 1-continued

List of examples and EC$_{150}$ data of novel compounds

| Example | Structure | Name | EC$_{150}$ (uM) |
|---|---|---|---|
| 29 | 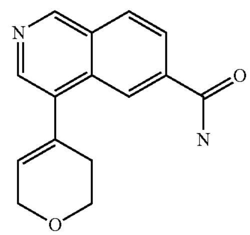 [SMILES: NC(=O)c1ccc2cncc(C3=CCOCC3)c2c1] | 4-(3,6-Dihydro-2H-pyran-4-yl)isoquinoline-6-carboxamide | 0.14 |
| 30 | 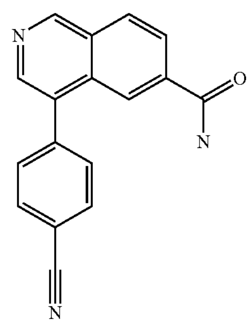 [SMILES: N#Cc1ccc(-c2cncc3ccc(C(N)=O)cc23)cc1] | 4-(4-Cyanophenyl)isoquinoline-6-carboxamide | 0.03 |
| 31 | 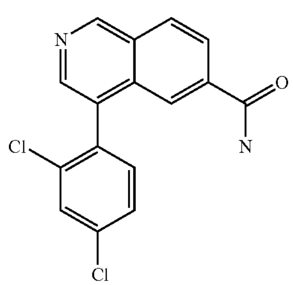 [SMILES: NC(=O)c1ccc2cncc(-c3ccc(Cl)cc3Cl)c2c1] | 4-(2,4-Dichlorophenyl)isoquinoline-6-carboxamide | 0.06 |
| 32 | 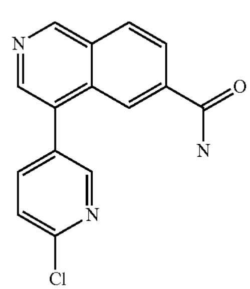 [SMILES: NC(=O)c1ccc2cncc(-c3ccc(Cl)nc3)c2c1] | 4-(6-Chloropyridin-3-yl)isoquinoline-6-carboxamide | 0.02 |

TABLE 2

List of examples and EC$_{150}$ data of known compounds

| 33 | 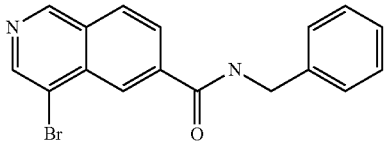 [SMILES: O=C(NCc1ccccc1)c1ccc2cncc(Br)c2c1] | 4-(4-Chlorophenyl)isoquinoline-6-carboxamide<br>CAS 1248555-68-1<br>WO2010116915 | 0.01 |
|---|---|---|---|
| 34 | | 4-(4-(Trifluoromethyl)phenyl)isoquinoline-6-carboxamide<br>CAS 1248554-05-3<br>WO2010116915 | 0.02 |

EXAMPLE 1

N-Benzyl-4-(pyridin-4-yl)isoquinoline-6-carboxamide

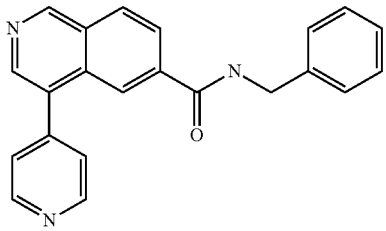

a) 4-Bromoisoquinoline-6-carboxylic acid

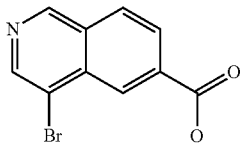

Isoquinoline-6-carboxylic acid (CAS106778-43-2, 100 mg, 577 µmol) was combined with acetic acid (3 ml) to give a light brown suspension. N-bromosuccinimide (123 mg, 693 µmol) was added. The reaction mixture was heated to 90° C., stirred for 2 hours and cooled to room temperature. The solid was filtered through sintered glass, washed with water (2×3 ml) and methanol (2×3 ml) and dried in vacuo to yield the title compound as brown solid (49 mg, 34%). MS: m/e=252.3, 254.3 [M+H]$^+$.

b) N-benzyl-4-bromoisoquinoline-6-carboxamide

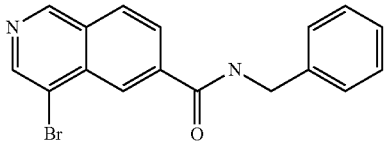 [SMILES: O=C(NCc1ccccc1)c1ccc2cncc(Br)c2c1]

A mixture of 4-bromoisoquinoline-6-carboxylic acid (250 mg, 992 µmol), N,N-diisopropylethylamine (156 mg, 211 µl, 1.21 mmol) and O-(7-azabenzotriazol-1-yl)-N,N,N',N'-tetramethyluronium hexafluorophosphate (HATU, 460 mg, 1.21 mmol) in dimethylformamide (12.5 ml) was stirred at room temperature for 10 minutes. Phenylmethanamine (106 mg, 108 µl, 992 µmol) was added and stirring was continued for 72 hours. Extraction with water/ethyl acetate and chromatography (silica gel, ethyl acetate/heptane=30:70 to 100:0) yielded the title compound as yellow solid (306 mg, 90%). MS: m/e=341.2, 343.3 [M+H]$^+$.

c) N-Benzyl-4-(pyridin-4-yl)isoquinoline-6-carboxamide

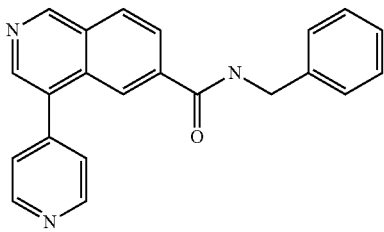 [SMILES: O=C(NCc1ccccc1)c1ccc2cncc(-c3ccncc3)c2c1]

To a suspension of N-benzyl-4-bromoisoquinoline-6-carboxamide (150 mg, 440 µmol) and pyridin-4-ylboronic acid (54.0 mg, 440 µmol) and cesium carbonate (158 mg, 484 µmol) in dioxane (20 ml) and water (2 ml) was added bis(diphenylphosphino)ferrocene-palladium(II)dichloride (16.1 mg, 22.0 µmol). The mixture was stirred at 80° C. for 3 hours. Removal of the solvent by distillation and chromatography (silica gel, ethyl acetate/heptane=50:50 to 100:0) and trituration with diethyl ether/pentane yielded the title compound as light brown solid (117 mg, 78%). MS: m/e=340.4 [M+H]$^+$.

EXAMPLE 2

N-benzyl-4-(4-chlorophenyl)isoquinoline-6-carboxamide

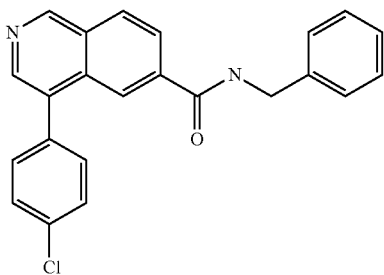 [SMILES: O=C(NCc1ccccc1)c1ccc2cncc(-c3ccc(Cl)cc3)c2c1]

To a suspension of N-benzyl-4-bromoisoquinoline-6-carboxamide (150 mg, 440 µmol) and 4-chlorophenylboronic acid (68.7 mg, 440 µmol) and cesium carbonate (158 mg, 484 µmol) in dioxane (20 ml) and water (2 ml) was added bis(diphenylphosphino)ferrocene-palladium(II)dichloride (16.1 mg, 22.0 µmol). The mixture was stirred at 80° C. for 3 hours. Removal of the solvent by distillation and chromatography (silica gel, ethyl acetate/heptane=50:50 to 100:0) and trituration with diethyl ether/pentane yielded the title compound as light brown solid (117 mg, 71%). MS: m/e=373.3 [M+H]$^+$.

EXAMPLE 3

[4-(4-Chloro-phenyl)-isoquinolin-6-yl]-(1,1-dioxo-thiomorpholin-4-yl)-methanone

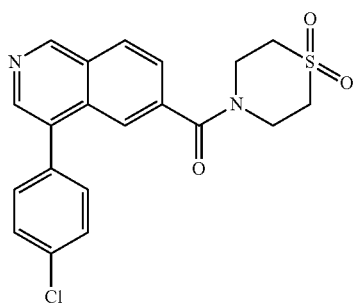 [SMILES: O=C(c1ccc2cncc(-c3ccc(Cl)cc3)c2c1)N1CCS(=O)(=O)CC1]

a) 4-(4-Chlorophenyl)isoquinoline-6-carboxylic acid

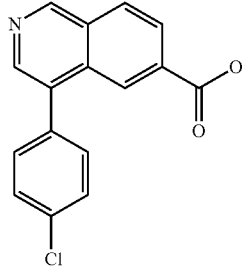

To a suspension of 4-bromoisoquinoline-6-carboxylic acid (1.25 g, 4.96 mmol) and 4-chlorophenylboronic acid (775 mg, 4.96 mmol) and cesium carbonate (1.78 g, 5.45 mmol) in dioxane (35 ml) and water (3.5 ml) was added bis(diphenylphosphino)ferrocene-palladium(II)dichloride (181 mg, 248 µmol). The mixture was stirred at 80° C. for 4 hours. Removal of the solvent by distillation, extraction with ethyl acetate/water (pH=3-4) and trituration with diethyl ether/pentane yielded the title compound as grey solid (1.23 g, 87%). MS: m/e=282.3 [M−H]$^-$.

b) [4-(4-Chloro-phenyl)-isoquinolin-6-yl]-(1,1-dioxo-thiomorpholin-4-yl)-methanone

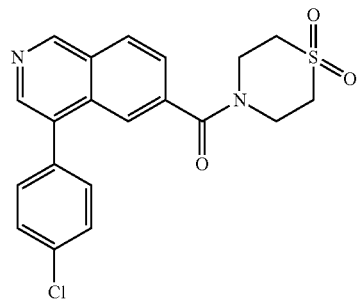

A mixture of 4-(4-chlorophenyl)isoquinoline-6-carboxylic acid (70 mg, 247 µmol), N,N-diisopropylethylamine (38.9 mg, 52.6 µl, 301 µmol) and O-(7-azabenzotriazol-1-yl)-N,N,N',N'-tetramethyluronium hexafluorophosphate (HATU, 114 mg, 301 µmol) in dimethylformamide (2 ml) was stirred at room temperature for 1 hour. Thiomorpholine 1,1-dioxide (36.7 mg, 271 µmol) was added and stirring was continued overnight. Extraction with water/ethyl acetate and chromatography (silica gel, ethyl acetate/heptane=50:50 to 100:0; then HPLC, C18 reverse phase, methanol/water (0.1% formic acid)=30:70 to 98:2) yielded the title compound as light yellow solid (35 mg, 35%). MS: m/e=401.3 [M+H]$^+$.

EXAMPLE 4

4-(4-Chloro-phenyl)-isoquinoline-6-carboxylic acid (2,2-dimethyl-propyl)-amide

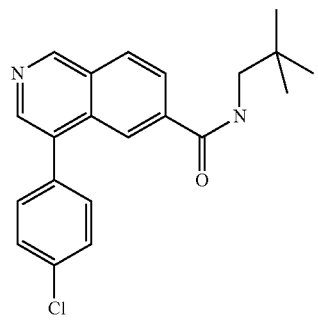

A mixture of 4-(4-chlorophenyl)isoquinoline-6-carboxylic acid (70 mg, 247 µmol), N,N-diisopropylethylamine (38.9 mg, 52.6 µl, 301 µmol) and O-(7-azabenzotriazol-1-yl)-N,N,N',N'-tetramethyluronium hexafluorophosphate (HATU, 114 mg, 301 µmol) in dimethylformamide (2 ml) was stirred at room temperature for 1 hour. 2,2-Dimethyl-propan-1-amine (21.5 mg, 28.5 µl, 247 µmol) was added and stirring was continued for 3 hours. Removal of the solvent by distillation and chromatography (silica gel, ethyl acetate/heptane=50:50 to 100:0; then HPLC, C18 reverse phase, methanol/water (0.1% formic acid)=30:70 to 98:2) yielded the title compound as off-white solid (57 mg, 66%). MS: m/e=353.4 [M+H]$^+$.

EXAMPLE 5

4-(4-Chlorophenyl)-N-cyclopropylisoquinoline-6-carboxamide

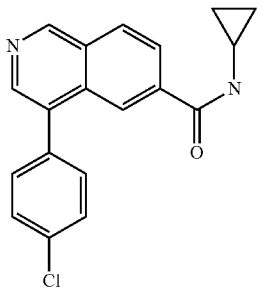 [SMILES: O=C(NC1CC1)c1ccc2cncc(-c3ccc(Cl)cc3)c2c1]

A mixture of 4-(4-chlorophenyl)isoquinoline-6-carboxylic acid (70 mg, 247 μmol), N,N-diisopropylethylamine (38.9 mg, 52.6 μl, 301 μmol) and O-(7-azabenzotriazol-1-yl)-N,N,N',N'-tetramethyluronium hexafluorophosphate (HATU, 114 mg, 301 μmol) in dimethylformamide (2 ml) was stirred at room temperature for 1 hour. Cyclopropanamine (14.1 mg, 17.3 μl, 247 μmol) was added and stirring was continued for 3 hours. Removal of the solvent by distillation and chromatography (silica gel, ethyl acetate/heptane=50:50 to 100:0; then HPLC, C18 reverse phase, methanol/water (0.1% formic acid)=30:70 to 98:2) yielded the title compound as off-white solid (45 mg, 57%). MS: m/e=323.3 [M+H]$^+$.

EXAMPLE 6

4-(4-Chlorophenyl)-N-(cyclopropylmethyl)isoquinoline-6-carboxamide

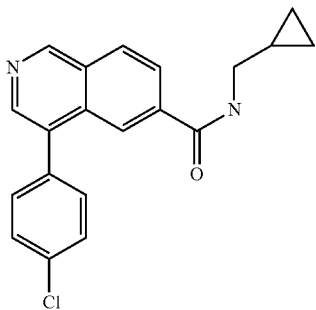

A mixture of 4-(4-chlorophenyl)isoquinoline-6-carboxylic acid (70 mg, 247 μmol), N,N-diisopropylethylamine (38.9 mg, 52.6 μl, 301 μmol) and O-(7-azabenzotriazol-1-yl)-N,N,N',N'-tetramethyluronium hexafluorophosphate (HATU, 114 mg, 301 μmol) in dimethylformamide (2 ml) was stirred at room temperature for 1 hour. Cyclopropylmethanamine (17.5 mg, 21.1 μl, 247 μmol) was added and stirring was continued over the weekend. Removal of the solvent by distillation, extraction with water/ethyl acetate and chromatography (HPLC, C18 reverse phase, methanol/water (0.1% formic acid)=30:70 to 98:2) yielded the title compound as light brown solid (41 mg, 49%). MS: m/e=337.4 [M+H]$^+$.

EXAMPLE 7

4-(4-Chlorophenyl)-N-(2-(methylsulfonyl)ethyl)isoquinoline-6-carboxamide

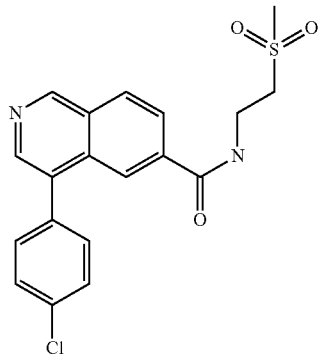 [SMILES: CS(=O)(=O)CCNC(=O)c1ccc2cncc(-c3ccc(Cl)cc3)c2c1]

A mixture of 4-(4-chlorophenyl)isoquinoline-6-carboxylic acid (70 mg, 247 μmol), N,N-diisopropylethylamine (38.9 mg, 52.6 μl, 301 μmol) and O-(7-azabenzotriazol-1-yl)-N,N,N',N'-tetramethyluronium hexafluorophosphate (HATU, 114 mg, 301 μmol) in dimethylformamide (2 ml) was stirred at room temperature for 1 hour. 2-(Methylsulfonyl)-ethanamine (30.4 mg, 247 μmol) was added and stirring was continued over the weekend. Removal of the solvent by distillation, extraction with water/ethyl acetate and chromatography (HPLC, C18 reverse phase, methanol/water (0.1% formic acid)=30:70 to 98:2) yielded the title compound as light brown solid (42 mg, 44%). MS: m/e=389.3 [M+H]$^+$.

EXAMPLE 8

4-(4-Chlorophenyl)-N-(pyridin-3-ylmethyl)isoquinoline-6-carboxamide

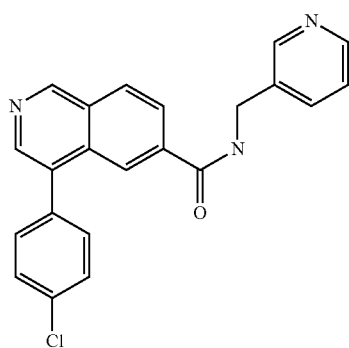 [SMILES: O=C(NCc1cccnc1)c1ccc2cncc(-c3ccc(Cl)cc3)c2c1]

A mixture of 4-(4-chlorophenyl)isoquinoline-6-carboxylic acid (70 mg, 247 μmol), N,N-diisopropylethylamine (38.9 mg, 52.6 μl, 301 μmol) and O-(7-azabenzotriazol-1-yl)-N,N,N',N'-tetramethyluronium hexafluorophosphate (HATU, 114 mg, 301 μmol) in dimethylformamide (2 ml) was stirred at room temperature for 1 hour. Pyridin-3-ylmethanamine (26.7 mg, 25.0 μl, 247 μmol) was added and stirring was continued overnight. Removal of the solvent by distillation, extraction with water/ethyl acetate and chromatography (HPLC, C18 reverse phase, methanol/water (0.1% formic acid)=30:70 to 98:2) yielded the title compound as light brown solid (52 mg, 56%). MS: m/e=374.4 [M+H]⁺.

EXAMPLE 9

4-(4-chlorophenyl)-N-(4-(methylsulfonyl)benzyl)isoquinoline-6-carboxamide

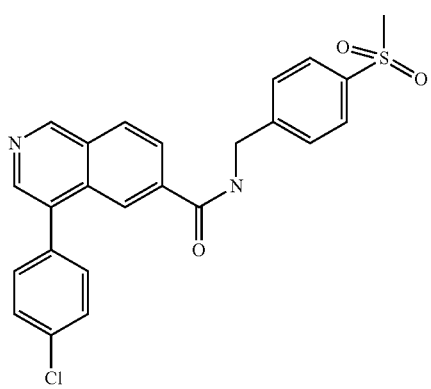 [SMILES: CS(=O)(=O)c1ccc(CNC(=O)c2ccc3cncc(-c4ccc(Cl)cc4)c3c2)cc1]

A mixture of 4-(4-chlorophenyl)isoquinoline-6-carboxylic acid (70 mg, 247 µmol), N,N-diisopropylethylamine (38.9 mg, 52.6 µl, 301 µmol) and O-(7-azabenzotriazol-1-yl)-N,N,N',N'-tetramethyluronium hexafluorophosphate (HATU, 114 mg, 301 µmol) in dimethylformamide (2 ml) was stirred at room temperature for 1 hour. (4-(Methylsulfonyl)-phenyl)methanamine (45.7 mg, 247 µmol) was added and stirring was continued overnight. Removal of the solvent by distillation, extraction with water/ethyl acetate and chromatography (HPLC, C18 reverse phase, methanol/water (0.1% formic acid)=30:70 to 98:2) yielded the title compound as light brown solid (43 mg, 39%). MS: m/e=451.4 [M+H]⁺.

EXAMPLE 10

4-(4-Chlorophenyl)-N-(2-methoxybenzyl)isoquinoline-6-carboxamide

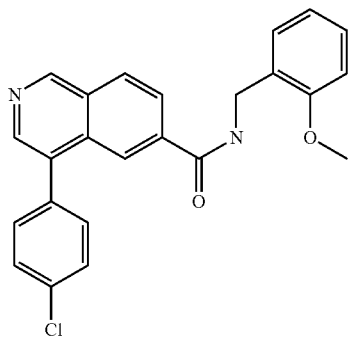 [SMILES: COc1ccccc1CNC(=O)c1ccc2cncc(-c3ccc(Cl)cc3)c2c1]

The synthesis was conducted in flow. Reagent solution A contained 4-(4-chlorophenyl)isoquinoline-6-carboxylic acid (10 mg, 35.2 µmol), O-(benzotriazol-1-yl)-N,N,N',N'-tetramethyluronium tetrafluoroborate (TBTU, 13.6 mg, 42.3 µmol) and N,N-diisopropylethylamine (13.7 mg, 18.5 µl, 106 µmol) in dimethylformamide (230 µl) and reagent solution B contained (2-methoxyphenyl)methanamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 100° C. for 5 min in a 10 ml PFA tube reactor coil. The crude product stream was purified in-line by preparative HPLC (C18 reverse phase, acetonitrile/water (0.05% formic acid)=2:98 to 98:2) to yield the title compound as an off-white solid (7.6 mg, 54%). MS: m/e=403.5 [M+H]⁺.

EXAMPLE 11

4-(4-Chlorophenyl)-N-(pyridin-2-ylmethyl)isoquinoline-6-carboxamide

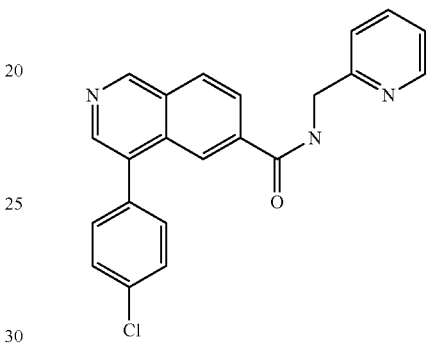

The synthesis was conducted in flow. Reagent solution A contained 4-(4-chlorophenyl)isoquinoline-6-carboxylic acid (10 mg, 35.2 µmol), O-(benzotriazol-1-yl)-N,N,N',N'-tetramethyluronium tetrafluoroborate (TBTU, 13.6 mg, 42.3 µmol) and N,N-diisopropylethylamine (13.7 mg, 18.5 µl, 106 µmol) in dimethylformamide (230 µl) and reagent solution B contained pyridin-2-ylmethanamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)= 2:98 to 98:2) to yield the title compound as a white solid (7.9 mg, 56%). MS: m/e=374.4 [M+H]⁺.

EXAMPLE 12

4-(4-Chlorophenyl)-N-(3-(methylsulfonyl)benzyl)isoquinoline-6-carboxamide

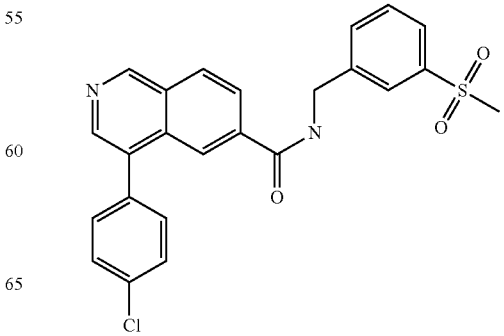

The synthesis was conducted in flow. Reagent solution A contained 4-(4-chlorophenyl)isoquinoline-6-carboxylic acid (10 mg, 35.2 µmol), O-(benzotriazol-1-yl)-N,N,N',N'-tetramethyluronium tetrafluoroborate (TBTU, 13.6 mg, 42.3 µmol) and N,N-diisopropylethylamine (13.7 mg, 18.5 µl, 106 µmol) in dimethylformamide (230 µl) and reagent solution B contained (3-(methylsulfonyl)phenyl)methanamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a white solid (6.3 mg, 44%). MS: m/e=451.4 [M+H]⁺.

EXAMPLE 13

4-(4-Chlorophenyl)-N-phenylisoquinoline-6-carboxamide

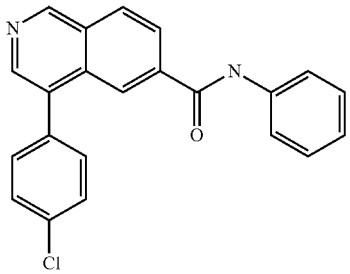 [SMILES: O=C(Nc1ccccc1)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained aniline (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a white solid (5.1 mg, 36%). MS: m/e=359.4 [M+H]⁺.

EXAMPLE 14

4-(4-Chlorophenyl)-N-(2,2,2-trifluoroethyl)isoquinoline-6-carboxamide

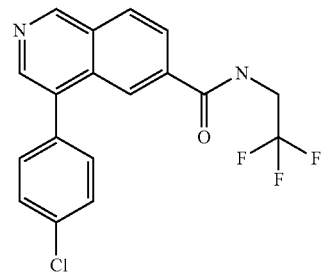

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained 2,2,2-trifluoro-ethylamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2: 98 to 98:2) to yield the title compound as a white solid (5.9 mg, 42%). MS: m/e=365.4 [M+H]⁺.

EXAMPLE 15

4-(4-Chlorophenyl)-N-isopropylisoquinoline-6-carboxamide

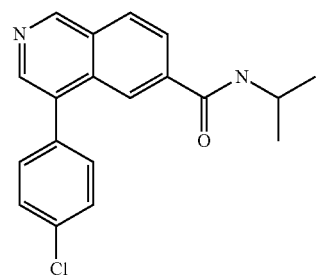 [SMILES: CC(C)NC(=O)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained isopropylamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a light brown oil (3.4 mg, 24%). MS: m/e=325.4 [M+H]$^+$.

EXAMPLE 16

4-(4-Chlorophenyl)-N-(tetrahydrofuran-3-yl)isoquinoline-6-carboxamide

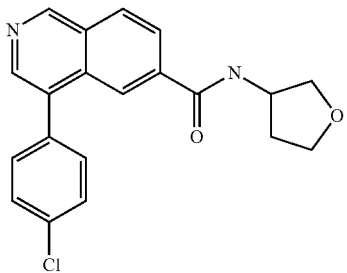 [SMILES: O=C(NC1CCOC1)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained tetrahydrofuran-3-ylamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a colorless oil (2.2 mg, 16%). MS: m/e=353.4 [M+H]$^+$.

EXAMPLE 17

4-(4-Chlorophenyl)-N-(1-hydroxy-2-methylpropan-2-yl)isoquinoline-6-carboxamide

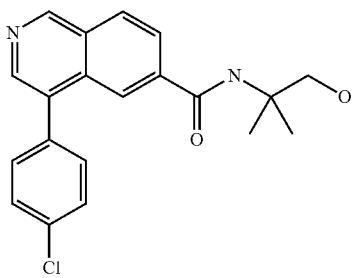 [SMILES: CC(C)(CO)NC(=O)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained 2-amino-2-methyl-propan-1-ol (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a colorless oil (6.2 mg, 44%). MS: m/e=355.4 [M+H]$^+$.

EXAMPLE 18

(4-(4-Chlorophenyl)isoquinolin-6-yl)(morpholino)methanone

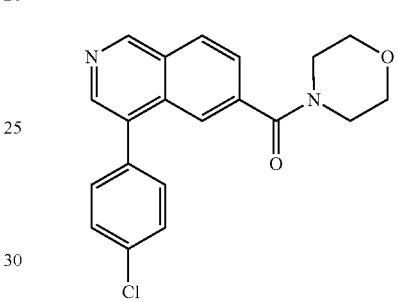

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained morpholine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a light brown oil (6.4 mg, 45%). MS: m/e=353.4 [M+H]$^+$.

EXAMPLE 19

(4-(4-Chlorophenyl)isoquinolin-6-yl)(4-methylpiperazin-1-yl)methanone

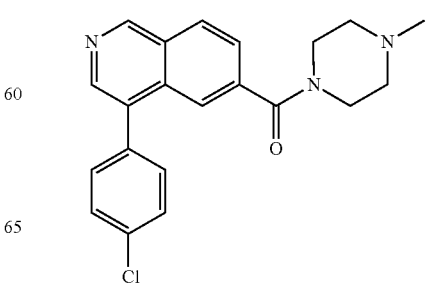

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained 1-methyl-piperazine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a colorless oil (6.0 mg, 42%). MS: m/e=366.5 [M+H]+.

EXAMPLE 20

4-(4-Chlorophenyl)-N-((2-methyl-5-oxopyrrolidin-2-yl)methyl)isoquinoline-6-carboxamide

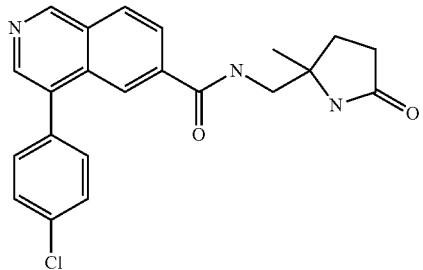 [SMILES: CC1(CNC(=O)c2ccc3cncc(-c4ccc(Cl)cc4)c3c2)CCC(=O)N1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained 5-aminomethyl-5-methyl-pyrrolidin-2-one (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as a white solid (4.0 mg, 28%). MS: m/e=394.0 [M+H]+.

EXAMPLE 21

4-(4-Chlorophenyl)-N-(cyclopropylmethyl)-N-methylisoquinoline-6-carboxamide

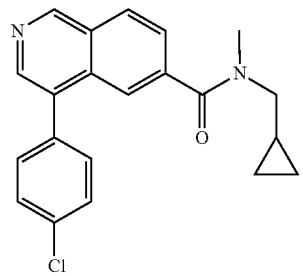 [SMILES: CN(CC1CC1)C(=O)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained cyclopropylmethyl-methyl-amine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)= 2:98 to 98:2) to yield the title compound as a colorless oil (2.5 mg, 18%). MS: m/e=351.0 [M+H]+.

EXAMPLE 22

(4-(4-Chlorophenyl)isoquinolin-6-yl)(3-hydroxypyrrolidin-1-yl)methanone

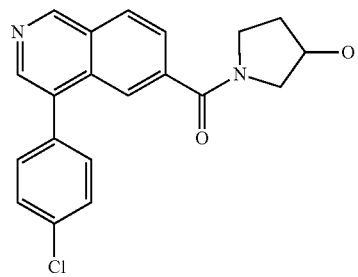 [SMILES: O=C(c1ccc2cncc(-c3ccc(Cl)cc3)c2c1)N1CCC(O)C1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained pyrrolidin-3ol (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as an off-white solid (6.9 mg, 49%). MS: m/e=352.9 [M+H]$^+$.

EXAMPLE 23

N-tert-Butyl-4-(4-chlorophenyl)isoquinoline-6-carboxamide

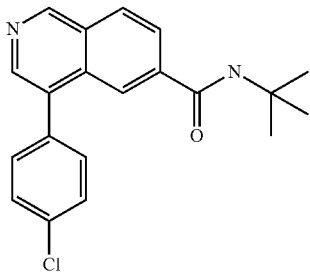 [SMILES: CC(C)(C)NC(=O)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 μmol), O-(benzotriazol-1-yl)-N,N,N',N'-tetramethyluronium tetrafluoroborate (TBTU, 10.9 mg, 33.8 μmol) and N,N-diisopropylethylamine (10.9 mg, 14.8 μl, 84.6 μmol) in dimethylformamide (230 μl) and reagent solution B contained tert-butylamine (106 μl of a 0.4 M stock solution in dimethylformamide, 42.3 μmol) in dimethylformamide (144 μl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as an off-white solid (5.3 mg, 37%). MS: m/e=339.0 [M+H]$^+$.

EXAMPLE 24

4-(4-Chlorophenyl)-N-(3,3,3-trifluoropropyl)isoquinoline-6-carboxamide

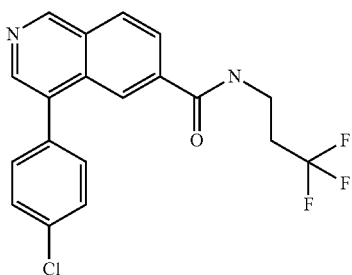 [SMILES: O=C(NCCC(F)(F)F)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 μmol), O-(benzotriazol-1-yl)-N,N,N',N'-tetramethyluronium tetrafluoroborate (TBTU, 10.9 mg, 33.8 μmol) and N,N-diisopropylethylamine (10.9 mg, 14.8 μl, 84.6 μmol) in dimethylformamide (230 μl) and reagent solution B contained 3,3,3-trifluoro-propylamine (106 μl of a 0.4 M stock solution in dimethylformamide, 42.3 μmol) in dimethylformamide (144 μl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as an off-white solid (5.9 mg, 42%). MS: m/e=379.4 [M+H]$^+$.

EXAMPLE 25

N'-(4-(4-Chlorophenyl)isoquinoline-6-carbonyl)methanesulfonohydrazide

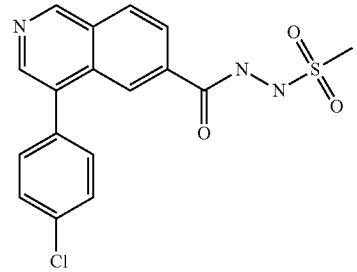 [SMILES: CS(=O)(=O)NNC(=O)c1ccc2cncc(-c3ccc(Cl)cc3)c2c1]

The synthesis was conducted in flow. Reagent solution A contained 4-(4-chlorophenyl)isoquinoline-6-carboxylic acid (8 mg, 28.2 μmol), O-(benzotriazol-1-yl)-N,N,N',N'-tetramethyluronium tetrafluoroborate (TBTU, 10.9 mg, 33.8 μmol) and N,N-diisopropylethylamine (10.9 mg, 14.8 μl, 84.6 μmol) in dimethylformamide (230 μl) and reagent solution B contained methanesulfonic acid hydrazide (106 μl of a 0.4 M stock solution in dimethylformamide, 42.3 μmol) in dimethylformamide (144 μl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)=2:98 to 98:2) to yield the title compound as an white solid (1.7 mg, 12%). MS: m/e=376.4 [M+H]$^+$.

EXAMPLE 26

4-(4-Chlorophenyl)-N-(1-methyl-1H-pyrazol-4-yl)isoquinoline-6-carboxamide

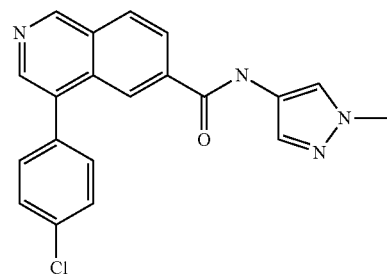 [SMILES: Cn1cc(NC(=O)c2ccc3cncc(-c4ccc(Cl)cc4)c3c2)cn1]

The synthesis was conducted in flow. Reagent solution A contained 4-(4-chlorophenyl)isoquinoline-6-carboxylic acid (8 mg, 28.2 µmol), O-(benzotriazol-1-yl)-N,N,N',N'-tetramethyluronium tetrafluoroborate (TBTU, 10.9 mg, 33.8 µmol) and N,N-diisopropylethylamine (10.9 mg, 14.8 µl, 84.6 µmol) in dimethylformamide (230 µl) and reagent solution B contained 1-methyl-1H-pyrazol-4-ylamine (106 µl of a 0.4 M stock solution in dimethylformamide, 42.3 µmol) in dimethylformamide (144 µl). The two reagent solutions were injected (0.250 mL of each solution) by means of Gilson LH 215 auto-sampler into the reactor sample loops (Gilson 819). Then, both reagent streams were combined at a T-piece connector and the reagent mixture heated at 120° C. for 5 min in a 10 ml PFA tube reactor coil. The crude product stream was purified in-line by preparative HPLC (C18 reverse phase, acetonitrile/water (0.05% triethylamine)= 2:98 to 98:2) to yield the title compound as an white solid (0.5 mg, 4%). MS: m/e=363.5 [M+H]+.

EXAMPLE 27

4-(4-Chlorophenyl)-N-(1-(3-(methylsulfonyl)phenyl)ethyl)isoquinoline-6-carboxamide

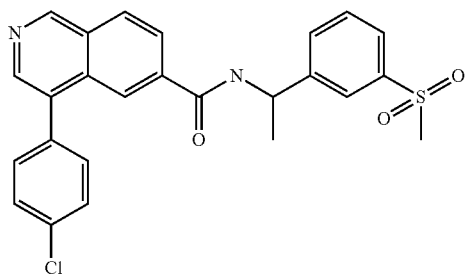 [SMILES: CC(NC(=O)c1ccc2cncc(-c3ccc(Cl)cc3)c2c1)c1cccc(S(C)(=O)=O)c1]

A mixture of 4-(4-chlorophenyl)isoquinoline-6-carboxylic acid (100 mg, 352 µmol), N, N-diisopropylethylamine (101 mg, 137 µl, 782 µmol) and O-(7-azabenzotriazol-1-yl)-N,N,N',N'-tetramethyluronium hexafluorophosphate (HATU, 164 mg, 430 µmol) in dimethylformamide (3 ml) was stirred at room temperature for 1 hour. 1-(3-(Methylsulfonyl)phenyl)ethanamine hydrochloride (83.1 mg, 352 µmol) was added and stirring was continued overnight. Removal of the solvent by distillation, extraction with water/ethyl acetate and chromatography (HPLC, C18 reverse phase, methanol/water (0.1% formic acid)=30:70 to 98:2) yielded the title compound as off-white solid (78 mg, 48%). MS: m/e=465.3 [M+H]+.

EXAMPLE 28

N'-(4-(4-Chlorophenyl)isoquinoline-6-carbonyl)-N-methylmethanesulfonohydrazide

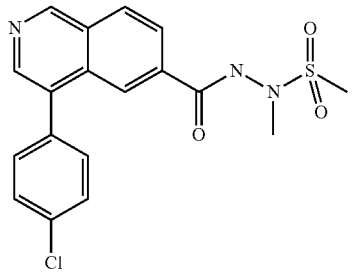 [SMILES: CN(NC(=O)c1ccc2cncc(-c3ccc(Cl)cc3)c2c1)S(C)(=O)=O]

a) N'-(4-Bromoisoquinoline-6-carbonyl)-N-methylmethanesulfonohydrazide

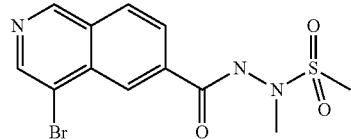 [SMILES: CN(NC(=O)c1ccc2cncc(Br)c2c1)S(C)(=O)=O]

A mixture of 4-bromoisoquinoline-6-carboxylic acid (300 mg, 1.19 mmol), N, N-diisopropylethylamine (341 mg, 461 µl, 2.64 mmol) and O-(7-azabenzotriazol-1-yl)-N,N,N',N'-tetramethyluronium hexafluorophosphate (HATU, 552 mg, 1.45 mmol) in dimethylformamide (4 ml) was stirred at room temperature for 1 hour. Methanesulfonic acid-1-methylhydrazide (148 mg, 1.19 mmol) was added and stirring was continued for 2 hours. Extraction with water/ethyl acetate and chromatography (silica gel, ethyl acetate/heptane=50:50 to 100:0) yielded the title compound as off-white solid 113 mg, 21%). MS: m/e=358.1, 360.3 [M+H]+.

b) N'-(4-(4-Chlorophenyl)isoquinoline-6-carbonyl)-N-methylmethanesulfonohydrazide

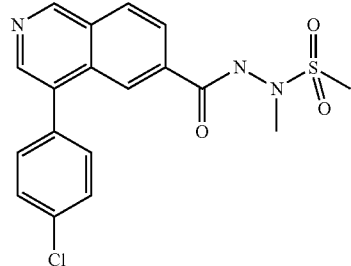 [SMILES: CN(NC(=O)c1ccc2cncc(-c3ccc(Cl)cc3)c2c1)S(C)(=O)=O]

To a suspension of N'-(4-bromoisoquinoline-6-carbonyl)-N-methylmethanesulfonohydrazide (100 mg, 223 µmol) and 4-chlorophenylboronic acid (34.9 mg, 223 µmol) and cesium carbonate (80.0 mg, 246 µmol) in dioxane (10 ml) and water (1 ml) was added bis(diphenylphosphino)ferrocene-palladium(II)dichloride (8.17 mg, 11.2 µmol). The mixture was stirred at 80° C. for 15 hours. Removal of the solvent by distillation and chromatography (silica gel, ethyl acetate/heptane=50:50 to 100:0) and trituration with diethyl ether/pentane yielded the title compound as off-white solid (47 mg, 54%). MS: m/e=390.3 [M+H]+.

EXAMPLE 29

4-(3,6-Dihydro-2H-pyran-4-yl)isoquinoline-6-carboxamide

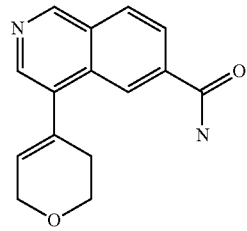

a) 4-Bromoisoquinoline-6-carboxamide

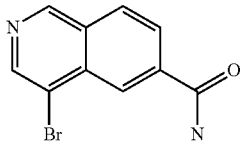 [SMILES: NC(=O)c1ccc2cncc(Br)c2c1]

A mixture of 4-bromoisoquinoline-6-carboxylic acid (500 mg, 1.98 mmol), 1,1'-carbonyldiimidazole (354 mg, 2.18 mmol) in dichloromethane (20 ml) was stirred at room temperature for 30 minutes. The solvent was removed by distillation and the residue was dissolved in dioxane (20 ml). Ammonium chloride (531 mg, 9.92 mmol) and triethyl amine (1.00 g, 1.37 ml, 9.92 mmol) was added and stirring was continued overnight. Extraction with water/ethyl acetate and trituration with diethyl ether/ethyl acetate yielded the title compound as off-white solid (304 mg, 61%). MS: m/e=251.2, 253.2 [M+H]$^+$.

b) 4-(3,6-Dihydro-2H-pyran-4-yl)isoquinoline-6-carboxamide

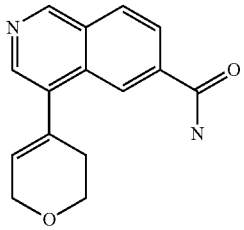 [SMILES: NC(=O)c1ccc2cncc(C3=CCOCC3)c2c1]

To a suspension of 4-bromoisoquinoline-6-carboxamide (100 mg, 398 μmol) and 2-(3,6-dihydro-2H-pyran-4-yl)-4,4,5,5-tetramethyl-1,3,2-dioxaborolane (83.7 mg, 398 μmol) and cesium carbonate (143 mg, 438 μmol) in dioxane (3 ml) and water (0.75 ml) was added bis(diphenylphosphino)ferrocene-palladium(II)dichloride (14.6 mg, 19.9 μmol). The mixture was stirred at 80° C. for 30 minutes. Removal of the solvent by distillation and chromatography (silica gel, ethyl acetate/heptane=50:50 to 100:0) yielded the title compound as light brown solid (75 mg, 74%). MS: m/e=255.4 [M+H]$^+$.

EXAMPLE 30

4-(4-Cyanophenyl)isoquinoline-6-carboxamide

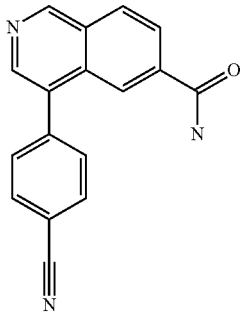

To a suspension of 4-bromoisoquinoline-6-carboxamide (50.0 mg, 199 μmol) and 4-(4,4,5,5-tetramethyl-1,3,2-dioxaborolan-2-yl)benzonitrile (45.6 mg, 199 μmol) and cesium carbonate (71.4 mg, 219 μmol) in dioxane (10 ml) and water (1 ml) was added bis(diphenylphosphino)ferrocene-palladium(II)dichloride (7.29 mg, 9.96 μmol). The mixture was stirred at 80° C. for 2 hours. Removal of the solvent by distillation and chromatography (silica gel, ethyl acetate/heptane=50:50 to 100:0) yielded the title compound as an off-white solid (52 mg, 96%). MS: m/e=274.4 [M+H]$^+$.

EXAMPLE 31

4-(2,4-Dichlorophenyl)isoquinoline-6-carboxamide

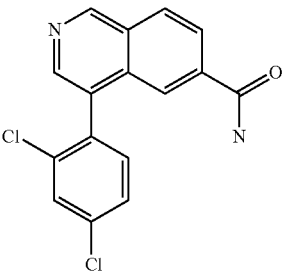 [SMILES: NC(=O)c1ccc2cncc(-c3ccc(Cl)cc3Cl)c2c1]

To a suspension of 4-bromoisoquinoline-6-carboxamide (50.0 mg, 199 μmol) and 2,4-dichlorophenylboronic acid (38.0 mg, 199 μmol) and cesium carbonate (71.4 mg, 219 μmol) in dioxane (10 ml) and water (1 ml) was added bis(diphenylphosphino)ferrocene-palladium(II)dichloride (7.29 mg, 9.96 μmol). The mixture was stirred at 80° C. for 2 hours. Removal of the solvent by distillation and chromatography (silica gel, ethyl acetate/heptane=50:50 to 100:0) yielded the title compound as an off-white solid (62 mg, 98%). MS: m/e=317.3, 319.3 [M+H]$^+$.

EXAMPLE 32

4-(6-Chloropyridin-3-yl)isoquinoline-6-carboxamide

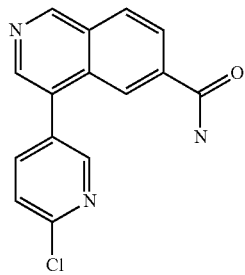 [SMILES: NC(=O)c1ccc2cncc(-c3ccc(Cl)nc3)c2c1]

To a suspension of 4-bromoisoquinoline-6-carboxamide (50.0 mg, 199 μmol), 6-chloropyridin-3-ylboronic acid (31.3 mg, 199 μmol) and cesium carbonate (71.4 mg, 219 μmol) in dioxane (10 ml) and water (1 ml) was added bis(diphenylphosphino)ferrocene-palladium(II)dichloride (7.29 mg, 9.96 μmol). The mixture was stirred at 80° C. for 2 hours. Removal of the solvent by distillation and chromatography (silica gel, ethyl acetate/heptane=50:50 to 100:0) yielded the title compound as an off-white solid (44 mg, 67%). MS: m/e=284.3 [M+H]$^+$.

EXAMPLE 33

4-(4-Chlorophenyl)isoquinoline-6-carboxamide (CAS1248555-68-1)

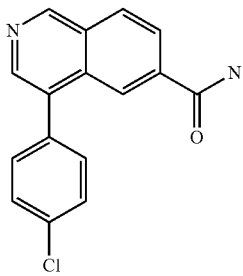 [SMILES: NC(=O)c1ccc2cncc(-c3ccc(Cl)cc3)c2c1]

A mixture of 4-(4-chlorophenyl)isoquinoline-6-carboxylic acid (100 mg, 352 μmol) and 1,1'-carbonyldiimidazole (62.9 mg, 388 μmol) in dichloromethane (5 ml) was stirred at room temperature for 30 minutes. A solution of ammonia in methanol (55.4 μl, 388 μmol) was added and stirring was continued overnight. Extraction with water (pH14)/ethyl acetate and chromatography (silica gel, ethyl acetate/heptane=50:50 to 100:0) and trituration with diethyl ether/pentane yielded the title compound as off-white solid (45 mg, 45%). MS: m/e=283.3 [M+H]$^+$.

EXAMPLE 34

4-(4-(Trifluoromethyl)phenyl)isoquinoline-6-carboxamide (CAS1248554-05-3)

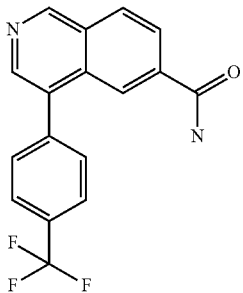 [SMILES: NC(=O)c1ccc2cncc(-c3ccc(C(F)(F)F)cc3)c2c1]

To a suspension of 4-bromoisoquinoline-6-carboxamide (60 mg, 239 μmol), 4-(trifluoromethyl)phenylboronic acid (45.4 mg, 239 μmol) and cesium carbonate (85.6 mg, 263 μmol) in dioxane (9 ml) and water (0.9 ml) was added bis(diphenylphosphino)ferrocene-palladium(II)dichloride (8.74 mg, 11.9 μmol). The mixture was stirred at 80° C. for 2 hours. Removal of the solvent by distillation and chromatography (silica gel, ethyl acetate/heptane=50:50 to 100:0) yielded the title compound as an off-white solid (62 mg, 82%). MS: m/e=317.4 [M+H]$^+$.

We claim:

1. A method for the therapeutic treatment of depression, anxiety disorders, Parkinson's disease, dementia, Alzheimer's disease, Down syndrome, autism spectrum disorders, amyotrophic lateral sclerosis, multiple sclerosis and Huntington's disease, comprising administering to a patient in need thereof a therapeutically effective amount of a compound according formula (I)

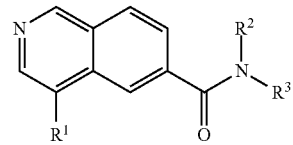

wherein
  $R^1$ is phenyl or pyridinyl, which are optionally substituted by halogen, cyano or lower alkyl substituted by halogen, or is dihydro-pyran-4-yl;
  $R^2$ is hydrogen or lower alkyl;
  $R^3$ is —(CHR)$_n$-phenyl, optionally substituted by lower alkoxy or S(O)$_2$-lower alkyl,
    or is heterocycloalkyl, optionally substituted by =O and lower alkyl, or,
    is —(CH$_2$)$_n$-five or six membered heteroaryl, optionally substituted by lower alkyl,
    or is hydrogen, lower alkyl, lower alkyl substituted by halogen, lower alkyl substituted by hydroxy, —NR—S(O)$_2$-lower alkyl, —(CH$_2$)$_n$-cycloalkyl or —(CH$_2$)$_n$—S(O)$_2$-lower alkyl; or,
  $R^2$ and $R^3$ form together with the N-atom to which they are attached a heterocycloalkyl ring, selected from the group consisting of 1,1-dioxo-thiomorpholinyl, morpholinyl, or pyrrolidinyl, optionally substituted by hydroxy;
  R is hydrogen or lower alkyl;
  n is 0, 1 or 2;
or, a pharmaceutically acceptable acid addition salt, or an enantiomer, a diastereomer or a mixture of enantiomers or diastereomers.

2. The method of claim 1 wherein the compound is selected from the group consisting of:
  N-benzyl-4-(pyridin-4-yl)isoquinoline-6-carboxamide,
  N-benzyl-4-(4-chlorophenyl)isoquinoline-6-carboxamide,
  [4-(4-chloro-phenyl)-isoquinolin-6-yl]-(1,1-dioxo-thiomorpholin-4-yl)-methanone,
  4-(4-chloro-phenyl)-isoquinoline-6-carboxylic acid (2,2-dimethyl-propyl)-amide,
  4-(4-chlorophenyl)-N-cyclopropylisoquinoline-6-carboxamide,
  4-(4-chlorophenyl)-N-(cyclopropylmethyl)isoquinoline-6-carboxamide,
  4-(4-chlorophenyl)-N-(2-(methylsulfonyl)ethyl)isoquinoline-6-carboxamide,
  4-(4-chlorophenyl)-N-(pyridin-3-ylmethyl)isoquinoline-6-carboxamide,
  4-(4-chlorophenyl)-N-(4-(methylsulfonyl)benzyl)isoquinoline-6-carboxamide,
  4-(4-chlorophenyl)-N-(2-methoxybenzyl)isoquinoline-6-carboxamide,
  4-(4-chlorophenyl)-N-(pyridin-2-ylmethyl)isoquinoline-6-carboxamide,
  4-(4-chlorophenyl)-N-(3-(methylsulfonyl)benzyl)isoquinoline-6-carboxamide,
  4-(4-chlorophenyl)-N-phenylisoquinoline-6-carboxamide,
  4-(4-chlorophenyl)-N-(2,2,2-trifluoroethyl)isoquinoline-6-carboxamide,
  4-(4-chlorophenyl)-N-isopropylisoquinoline-6-carboxamide,
  4-(4-chlorophenyl)-N-(tetrahydrofuran-3-yl)isoquinoline-6-carboxamide, 4-(4-chlorophenyl)-N-(1-hydroxy-2-methylpropan-2-yl)isoquinoline-6-carboxamide,
(4-(4-chlorophenyl)isoquinolin-6-yl)(morpholino)methanone,
(4-(4-chlorophenyl)isoquinolin-6-yl)(4-methylpiperazin-1-yl)methanone,
4-(4-chlorophenyl)-N-((2-methyl-5-oxopyrrolidin-2-yl)methyl)isoquinoline-6-carboxamide,
4-(4-chlorophenyl)-N-(cyclopropylmethyl)-N-methylisoquinoline-6-carboxamide, (4-(4-chlorophenyl)isoquinolin-6-yl)(3-hydroxypyrrolidin-1-yl)methanone,
N-tert-butyl-4-(4-chlorophenyl)isoquinoline-6-carboxamide,
4-(4-chlorophenyl)-N-(3,3,3-trifluoropropyl)isoquinoline-6-carboxamide,
N'-(4-(4-chlorophenyl)isoquinoline-6-carbonyl)methanesulfonohydrazide,
4-(4-chlorophenyl)-N-(1-methyl-1H-pyrazol-4-yl)isoquinoline-6-carboxamide,
4-(4-chlorophenyl)-N-(1-(3-(methylsulfonyl)phenyl)ethyl)isoquinoline-6-carboxamide,
N'-(4-(4-chlorophenyl)isoquinoline-6-carbonyl)-N-methylmethanesulfonohydrazide,
4-(3,6-dihydro-2H-pyran-4-yl)isoquinoline-6-carboxamide,
4-(4-cyanophenyl)isoquinoline-6-carboxamide,
4-(2,4-dichlorophenyl)isoquinoline-6-carboxamide,
4-(6-chloropyridin-3-yl)isoquinoline-6-carboxamide,
4-(4-chlorophenyl)isoquinoline-6-carboxamide (CAS1248555-68-1), and,
4-(4-(trifluoromethyl)phenyl)isoquinoline-6-carboxamide (CAS1248554-05-3), or,
or a pharmaceutically acceptable acid addition salt, pure enantiomer or a mixture of enantiomers thereof.

3. A compound according to formula I

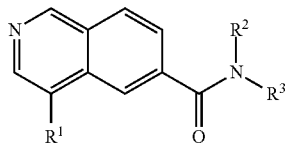

I wherein
R$^1$ is phenyl or pyridinyl, which are optionally substituted by halogen, cyano or lower alkyl substituted by halogen, or is dihydro-pyran-4-yl;
R$^2$ is hydrogen or lower alkyl;
R$^3$ is —(CHR)$_n$-phenyl, optionally substituted by lower alkoxy or S(O)$_2$-lower alkyl,
or is heterocycloalkyl, optionally substituted by =O and lower alkyl, or,
is —(CH$_2$)$_n$-five or six membered heteroaryl, optionally substituted by lower alkyl,
or is lower alkyl substituted by halogen, lower alkyl substituted by hydroxy, —NR—S(O)$_2$-lower alkyl, —(CH$_2$)$_n$-cycloalkyl or
—(CH$_2$)$_n$—S(O)$_2$-lower alkyl; or;
R$^2$ and R$^3$ form together with the N-atom to which they are attached a heterocycloalkyl ring,
selected from the group consisting of 1,1-dioxo-thiomorpholinyl, morpholinyl, or pyrrolidinyl, optionally substituted by hydroxy;
R is hydrogen or lower alkyl;
n is 0, 1 or 2; or,
a pharmaceutically acceptable acid addition salt, or an enantiomer, a diastereomer or a mixture of enantiomers or diastereomers thereof, with the proviso the compound is not:
4-(4-chlorophenyl)isoquinoline-6-carboxamide (CAS1248555-68-1), or,
4-(4-(trifluoromethyl)phenyl)isoquinoline-6-carboxamide (CAS1248554-05-3).

4. The compound according to formula I-1

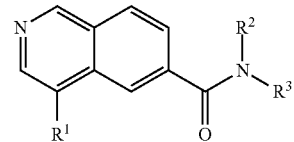

I-1 wherein
R$^1$ is pyridinyl, which is optionally substituted by halogen, cyano or lower alkyl substituted by halogen, or is dihydro-pyran-4-yl;
R$^2$ is hydrogen or lower alkyl;
R$^3$ is —(CHR)$_n$-phenyl, optionally substituted by lower alkoxy or S(O)$_2$-lower alkyl,
or is heterocycloalkyl, optionally substituted by =O and lower alkyl,
or is —(CH$_2$)$_n$-five or six membered heteroaryl, optionally substituted by lower alkyl,
or is hydrogen, lower alkyl, lower alkyl substituted by halogen, lower alkyl substituted by hydroxy, —NR—S(O)$_2$-lower alkyl, —(CH$_2$)$_n$-cycloalkyl or —(CH$_2$)$_n$—S(O)$_2$-lower alkyl; or
R$^2$ and R$^3$ form together with the N-atom to which they are attached a heterocycloalkyl ring, selected from the group consisting of 1,1-dioxo-thiomorpholinyl, morpholinyl, or pyrrolidinyl, optionally substituted by hydroxyl;
R is hydrogen or lower alkyl;
n is 0, 1 or 2; or,
a pharmaceutically acceptable acid addition salt, or an enantiomer, a diastereomer or a mixture of enantiomers or diastereomers thereof.

5. The compound of formula I-1 according to claim 4, which compound is:
N-benzyl-4-(pyridin-4-yl)isoquinoline-6-carboxamide,
4-(3,6-dihydro-2H-pyran-4-yl)isoquinoline-6-carboxamide, or,
4-(6-chloropyridin-3-yl)isoquinoline-6-carboxamide,
or a pharmaceutically acceptable salt thereof.

6. The compound of formula I-2 according to claim 3

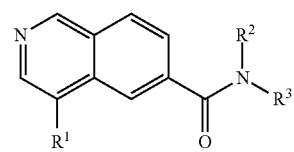

I-2 wherein
R$^1$ is phenyl or pyridinyl, which are optionally substituted by halogen, cyano or lower alkyl substituted by halogen, or is dihydro-pyran-4-yl;

$R^2$ and $R^3$ form together with the N-atom to which they are attached a heterocycloalkyl ring, selected from the group consisting of 1,1-dioxo-thiomorpholinyl, morpholinyl, or pyrrolidinyl, optionally substituted by hydroxyl;

R is hydrogen or lower alkyl;

n is 0, 1 or 2;

or a pharmaceutically acceptable acid addition salt, a racemic mixture or its corresponding enantiomer and/or optical isomers thereof.

7. The compound of formula I-2 according to claim 6, which compound is:

[4-(4-chloro-phenyl)-isoquinolin-6-yl]-(1,1-dioxo-thiomorpholin-4-yl)-methanone, (4-(4-chlorophenyl)isoquinolin-6-yl)(morpholino)methanone, (4-(4-chlorophenyl)isoquinolin-6-yl)(4-methylpiperazin-1-yl)methanone, or, (4-(4-chlorophenyl)isoquinolin-6-yl)(3-hydroxypyrrolidin-1-yl)methanone, or, a pharmaceutically acceptable salt thereof.

8. A pharmaceutical composition comprising a compound of formula I in claim 3 admixed with at least one pharmaceutically acceptable excipient carrier or diluent.

9. A process for preparation of a compound of formula I and their pharmaceutically acceptable salts according to claim 3, which process comprises a) reacting a compound of formula (1)

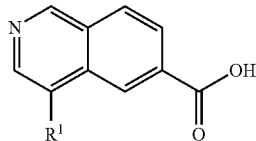

(1)

with a compound of formula (2)

$NHR^2R^3$ (2)

to afford a compound of formula I

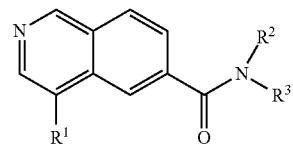

(I)

and, if desired, converting the compounds obtained into pharmaceutically acceptable acid addition salts, or b) reacting a compound of formula (3)

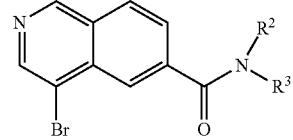

(3)

with a compound of formula (4)

$(HO)_2BR^1$ (4)

to afford a compound of formula I, and, if desired, converting the compounds obtained into pharmaceutically acceptable acid addition salts, wherein the substituents are as defined in claim 3.

* * * * *